(12) United States Patent
El-Kattan et al.

(10) Patent No.: US 10,662,160 B1
(45) Date of Patent: May 26, 2020

(54) CRYSTALLINE SALTS OF A PLASMA KALLIKREIN INHIBITOR

(71) Applicant: BioCryst Pharmaceuticals, Inc., Durham, NC (US)

(72) Inventors: Yahya El-Kattan, Vestavia Hills, AL (US); Yarlagadda S. Babu, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 16/671,649

(22) Filed: Nov. 1, 2019

Related U.S. Application Data

(60) Provisional application No. 62/754,983, filed on Nov. 2, 2018.

(51) Int. Cl.
  *C07D 231/14* (2006.01)
  *A61K 9/00* (2006.01)
  *A23L 33/10* (2016.01)

(52) U.S. Cl.
  CPC .......... *C07D 231/14* (2013.01); *A61K 9/0029* (2013.01); *A61K 9/0053* (2013.01); *A23L 33/10* (2016.08); *A23V 2002/00* (2013.01); *C07B 2200/13* (2013.01)

(58) Field of Classification Search
  None
  See application file for complete search history.

(56) References Cited

U.S. PATENT DOCUMENTS

| | | | |
|---|---|---|---|
| 4,559,157 A * | 12/1985 | Smith | A45D 37/00 106/8 |
| 9,206,146 B2 | 12/2015 | Langner et al. | |
| 10,125,102 B2 * | 11/2018 | Kotian | C07D 401/14 |
| 10,329,260 B2 | 6/2019 | Kotian et al. | |
| 2018/0354906 A1 | 12/2018 | Kotian et al. | |
| 2019/0322626 A1 | 10/2019 | Kotian et al. | |

FOREIGN PATENT DOCUMENTS

WO  WO-2015/134998 A1  9/2015

OTHER PUBLICATIONS

Aygoren et al., "BCX7353: An Effective and Safe Oral Prophylaxis Against Attacks of Hereditary Angioedema. APeX-1 Final Results," BioCryst Pharmaceuticals, Presented at ACAAI (2017).
Aygören-Pürsün et al., "Oral Plasma Kallikrein Inhibitor for Prophylaxis in Hereditary Angioedema," The New England Journal of Medicine, 379(4):352-362 (2018).
Aygören-Pürsün, "BCX7353, a Once-Daily Oral Kallikrein Inhibitor, is Effective and Safe in the Prophylaxis of Acute Attacks in Patients with Hereditary Angioedema: Results from the First Interim Analysis of the APeX-1 Study," Universitätsklinikum Frankfurt, 1-22 (2015).
International Search Report and Written Opinion for International Application No. PCT/US2019/059385 dated Jan. 17, 2020.

* cited by examiner

*Primary Examiner* — Kamal A Saeed
(74) *Attorney, Agent, or Firm* — Dana M. Gordon; Foley Hoag LLP

(57) ABSTRACT

Disclosed are crystalline salts of Compound I, methods of preparing them, and related pharmaceutical preparations thereof. Also disclosed are methods of treatment using the crystalline salts of the invention.

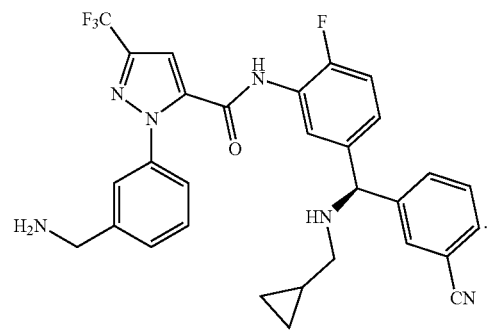

28 Claims, 3 Drawing Sheets

CRYSTALLINE SALTS OF A PLASMA KALLIKREIN INHIBITOR

RELATED APPLICATIONS

This application claims the benefit of priority to U.S. Provisional Patent Application Ser. No. 62/754,983, filed Nov. 2, 2018; the contents of which are hereby incorporated by reference.

BACKGROUND

Serine proteases make up the largest and most extensively studied group of proteolytic enzymes. Their critical roles in physiological processes extend over such diverse areas as blood coagulation, fibrinolysis, complement activation, reproduction, digestion, and the release of physiologically active peptides. Many of these vital processes begin with cleavage of a single peptide bond or a few peptide bonds in precursor protein or peptides. Sequential limited proteolytic reactions or cascades are involved in blood clotting, fibrinolysis, and complement activation. The biological signals to start these cascades can be controlled and amplified as well. Similarly, controlled proteolysis can shut down or inactivate proteins or peptides through single bond cleavages.

Kallikreins are a subgroup of serine proteases. In humans, plasma kallikrein (KLKB1) has no known homologue, while tissue kallikrein-related peptidases (KLKs) encode a family of fifteen closely related serine proteases. Plasma kallikrein participates in a number of pathways relating to the intrinsic pathway of coagulation, inflammation, and the complement system.

Coagulation is the process by which blood forms clots, for example to stop bleeding. The physiology of coagulation is somewhat complex insofar as it includes two separate initial pathways, which converge into a final common pathway leading to clot formation. In the final common pathway, prothrombin is converted into thrombin, which in turn converts fibrinogen into fibrin, the latter being the principal building block of cross-linked fibrin polymers which form a hemostatic plug. Of the two initial pathways upstream of the final common pathway, one is known as the contact activation or intrinsic pathway, and the other is known as the tissue factor or extrinsic pathway.

The intrinsic pathway begins with formation of a primary complex on collagen by high-molecular-weight kininogen (HMWK), prekallikrein, and FXII (Factor XII; Hageman factor). Prekallikrein is converted to kallikrein, and FXII is activated to become FXIIa. FXIIa then converts Factor XI (FXI) into FXIa, and FXIa in turn activates Factor IX (FIX), which with its co-factor FVIIIa form the "tenase" complex, which activates Factor X (FX) to FXa. It is FXa which is responsible for the conversion of prothrombin into thrombin within the final common pathway.

Prekallikrein, the inactive precursor of plasma kallikrein, is synthesized in the liver and circulates in the plasma bound to HMWK or as a free zymogen. Prekallikrein is cleaved by activated factor XII (FXIIa) to release activated plasma kallikrein (PK). Activated plasma kallikrein displays endopeptidase activity towards peptide bonds after arginine (preferred) and lysine. PK then generates additional FXIIa in a feedback loop which in turn activates factor XI (FXI) to FXIa to connect to the common pathway. Although the initial activation of the intrinsic pathway is through a small amount of FXIIa activating a small amount of PK, it is the subsequent feedback activation of FXII by PK that controls the extent of activation of the intrinsic pathway and hence downstream coagulation. Hathaway, W. E., et al. (1965) Blood 26:521-32.

Activated plasma kallikrein also cleaves HMWK to release the potent vasodilator peptide bradykinin. It is also able to cleave a number of inactive precursor proteins to generate active products, such as plasmin (from plasminogen) and urokinase (from prourokinase). Plasmin, a regulator of coagulation, proteolytically cleaves fibrin into fibrin degradation products that inhibit excessive fibrin formation.

Patients who have suffered acute myocardial infarction (MI) show clinical evidence of being in a hypercoagulable (clot-promoting) state. This hypercoagulability is paradoxically additionally aggravated in those receiving fibrinolytic therapy. Increased generation of thrombin, as measured by thrombin-antithrombin III (TAT) levels, is observed in patients undergoing such treatment compared to the already high levels observed in those receiving heparin alone. Hoffmeister, H. M. et al. (1998) Circulation 98:2527-33. The increase in thrombin has been proposed to result from plasmin-mediated activation of the intrinsic pathway by direct activation of FXII by plasmin.

Not only does the fibrinolysis-induced hypercoagulability lead to increased rates of reocclusion, but it is also probably responsible, at least in part, for failure to achieve complete fibrinolysis of the clot (thrombus), a major shortcoming of fibrinolytic therapy (Keeley, E. C. et al. (2003) Lancet 361: 13-20). Another problem in fibrinolytic therapy is the accompanying elevated risk of intracranial hemorrhage. Menon, V. et al. (2004) (Chest 126:549S-575S; Fibrinolytic Therapy Trialists' Collaborative Group (1994) Lancet 343: 311-22. Hence, an adjunctive anti-coagulant therapy that does not increase the risk of bleeding, but inhibits the formation of new thrombin, would be greatly beneficial.

Plasma kallikrein inhibitors also have therapeutic potential for treating hereditary angioedema (HAE). HAE is is a serious and potentially life-threatening rare genetic illness, caused by mutations in the C1-esterase inhibitor (C1INH) gene, located on chromosome 11q. HAE is inherited as an autosomal dominant condition, although one quarter of diagnosed cases arise from a new mutation. HAE has been classed as an orphan disease in Europe, with an estimated prevalence of 1 in 50,000. Individuals with HAE experience recurrent acute attacks of painful subcutaneous or submucosal edema of the face, larynx, gastrointestinal tract, limbs or genitalia which, if untreated, may last up to 5 days. Attacks vary in frequency, severity and location and can be life-threatening. Laryngeal attacks, with the potential for asphyxiation, pose the greatest risk. Abdominal attacks are especially painful, and often result in exploratory procedures or unnecessary surgery. Facial and peripheral attacks are disfiguring and debilitating.

HAE has a number of subtypes. HAE type I is defined by C1INH gene mutations which produce low levels of C1-inhibitor, whereas HAE type II is defined by mutations which produce normal levels of ineffective C1 protein. HAE type III has separate pathogenesis, being caused by mutations in the F12 gene which codes for the serine protease known as Factor XII. Diagnostic criteria for distinguishing the subtypes of HAE, and distinguishing HAE from other angioedemas, can be found in *Ann Allergy Asthma Immunol* 2008; 100(Suppl2): S30-S40 and *J Allergy Clin Immunol* 2004; 114: 629-37, incorporated herein by reference.

Current treatments for HAE fall into two main types. Older non-specific treatments including androgens and anti-fibrinolytics are associated with significant side effects, particularly in females. Newer treatments are based on an understanding of the molecular pathology of the disease, namely that C1INH is the most important inhibitor of kallikrein in human plasma and that C1INH deficiency leads to unopposed activation of the kallikrein-bradykinin cascade, with bradykinin the most important mediator of the locally increased vascular permeability that is the hallmark of an attack. All of the currently available targeted therapies are administered by intravenous or subcutaneous injection. There is currently no specific targeted oral chronic therapy for HAE.

Therefore, a need exists to develop inhibitors of PK that can tip the balance of fibrinolysis/thrombosis at the occluding thrombus toward dissolution, thereby promoting reperfusion and also attenuating the hypercoagulable state, thus preventing thrombus from reforming and reoccluding the vessel. In particular, the creation of plasma kallikrein inhibitors that are specific and capable of being formulated for in vivo use could lead to a new class of therapeutics. Thus, what is needed are improved compositions and methods for preparing and formulating plasma kallikrein inhibitors.

SUMMARY OF THE INVENTION

One aspect of the invention relates to a crystalline salt of Compound I,

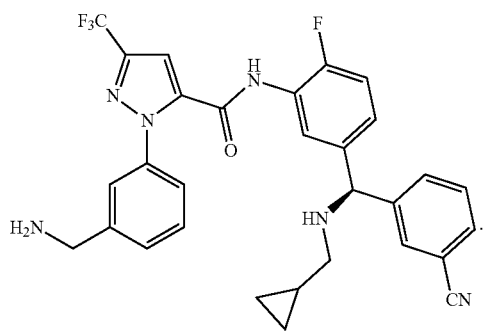

Another aspect of the invention relates to methods for preparing the crystalline salts of Compound I. In such aspects, the methods comprise a) providing a freebase mixture of Compound I in a first organic solvent; b) combining the freebase mixture with a reagent solution comprising an acid and a second organic solvent under conditions sufficient to form a mixture comprising a salt of Compound I; and c) crystallizing the salt of Compound I from the mixture comprising a salt of Compound I.

In certain embodiments, the present invention provides a pharmaceutical composition, comprising a crystalline salt of Compound I, and one or more pharmaceutically acceptable excipients. In certain embodiments, the pharmaceutical preparations may be for use in treating or preventing a condition or disease characterized by aberrant plasma kallikrein activity.

DETAILED DESCRIPTION OF THE INVENTION

Figure 1:
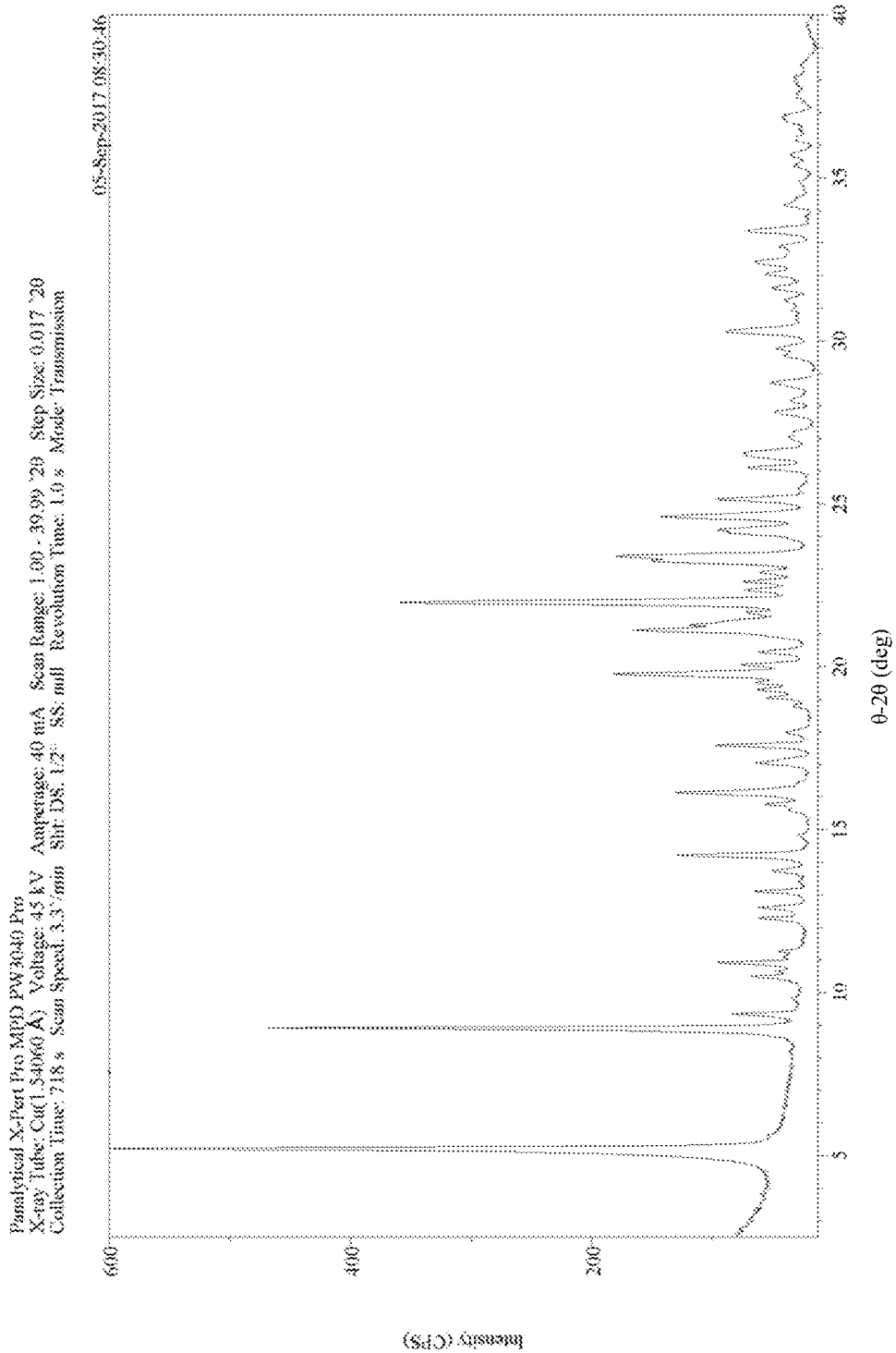
FIG. 1 is an X-ray powder diffraction (XRPD) pattern of Compound I•2(HCl).

In certain embodiments, the invention provides a crystalline salt of Compound I,

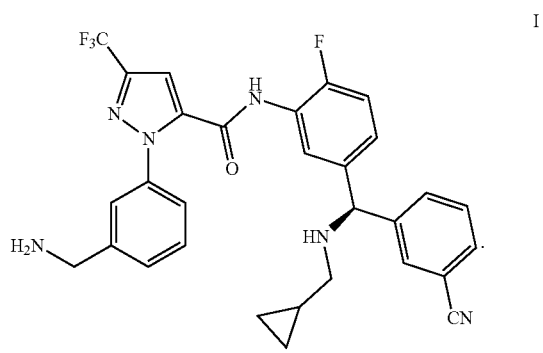 [SMILES: N#Cc1cccc([C@@H](NCC2CC2)c2ccc(F)c(NC(=O)c3cc(C(F)(F)F)nn3-c3cccc(CN)c3)c2)c1]

Compound I is a potent inhibitor of plasma kallikrein, described in WO 2015/134998 and U.S. Patent Application Publication No. 2017/0073314 A1, the contents of both of which are hereby incorporated by reference.

A crystalline form of Compound I can be used to modulate/improve the physicochemical properties of the compound, including but not limited to solid state properties (e.g., crystallinity, hygroscopicity, melting point, or hydration), pharmaceutical properties (e.g., solubility/dissolution rate, stability, or compatibility), as well as crystallization characteristics (e.g., purity, yield, or morphology). For example, crystallization of Compound I enables access to the compound with consistent and predictable purity levels. Additionally, the uniform particle sizes resulting from crystallization lead to improved processability of the solid crystalline compound relative to the solid amorphous form. The crystalline form of Compound I exhibits beneficial pharmacokinetic properties as well; the uniformity of the crystal form leads to a consistent and predictable pharmacokinetic profile.

In certain embodiments, the crystalline salt is a hydrochloride salt, e.g., a bis(hydrochloride) salt.

In certain embodiments, the polymorph of the crystalline salt is characterized by X-ray powder diffraction (XRPD). θ represents the diffraction angle, measured in degrees. In certain embodiments, the diffractometer used in XRPD measures the diffraction angle as two times the diffraction angle θ. Thus, in certain embodiments, the diffraction patterns described herein refer to X-ray intensity measured against angle 2θ.

The peak value at the diffraction angle θ, or at two times the diffraction angle θ (2θ), may exhibit a minor measurement error due to the XRPD instruments or the conditions under which the measurement is taken. Accordingly, in certain embodiments, the characteristic peaks in the XRPD pattern have a value of ° 2θ±0.2°. In certain embodiments, the characteristic peaks in the XRPD pattern have a value of ° 2θ±0.1°. In certain embodiments, the characteristic peaks in the XRPD pattern have a value of ° 2θ±0.06°.

In certain embodiments, the crystalline salt of Compound I has characteristic peaks in the X-ray powder diffraction (XRPD) pattern at values of two theta (° 2θ±0.2°) of 5.3, 9.0, and 22.0. In certain embodiments, the crystalline salt of Compound I has characteristic peaks in the X-ray powder diffraction (XRPD) pattern at values of two theta (° 2θ) of 5.3, 9.0, and 22.0.

In further embodiments, the crystalline salt has characteristic peaks in the X-ray powder diffraction (XRPD) pattern at values of two theta (° 2θ±0.2°) of 5.3, 9.0, 19.8, 21.2, 22.0, and 23.3. In certain embodiments, the crystalline salt has characteristic peaks in the X-ray powder diffraction (XRPD) pattern at values of two theta (° 2θ) of 5.3, 9.0, 19.8, 21.2, 22.0, and 23.3.

In yet further embodiments, the crystalline salt has characteristic peaks in the X-ray powder diffraction (XRPD) pattern at values of two theta (° 2θ±0.2°) of 5.3, 9.0, 14.3, 16.2, 19.8, 21.2, 22.0, 23.3, 24.6, and 30.3. In certain embodiments, the crystalline salt has characteristic peaks in the X-ray powder diffraction (XRPD) pattern at values of two theta (° 2θ) of 5.3, 9.0, 14.3, 16.2, 19.8, 21.2, 22.0, 23.3, 24.6, and 30.3.

In certain embodiments, the crystalline salt of Compound I has characteristic peaks in the X-ray powder diffraction (XRPD) pattern at values of two theta (° 2θ±0.2°) of 5.28, 8.96, and 22.01. In certain embodiments, the crystalline salt of Compound I has characteristic peaks in the X-ray powder diffraction (XRPD) pattern at values of two theta (° 2θ) of 5.28, 8.96, and 22.01.

In further embodiments, the crystalline salt has characteristic peaks in the X-ray powder diffraction (XRPD) pattern at values of two theta (° 2θ±0.2°) of 5.28, 8.96, 19.79, 21.16, 22.01, and 23.31. In certain embodiments, the crystalline salt of Compound I has characteristic peaks in the X-ray powder diffraction (XRPD) pattern at values of two theta (° 2θ) of 5.28, 8.96, 19.79, 21.16, 22.01, and 23.31.

In further embodiments, the crystalline salt has characteristic peaks in the X-ray powder diffraction (XRPD) pattern at values of two theta (° 2θ±0.2°) of 5.28, 8.96, 14.27, 16.18, 19.79, 21.16, 22.01, 23.31, 24.64, and 30.31. In certain embodiments, the crystalline salt of Compound I has characteristic peaks in the X-ray powder diffraction (XRPD) pattern at values of two theta (° 2θ) of 5.28, 8.96, 14.27, 16.18, 19.79, 21.16, 22.01, 23.31, 24.64, and 30.31.

In certain embodiments, the crystalline salt of Compound I has an XRPD pattern substantially similar to that shown in FIG. 1.

The relative intensity, as well as the two theta value, of each peak in the XRPD patterns described above, as well as shown in FIG. 1, may change or shift under certain conditions, although the crystalline form is the same. By comparing XRPD data sets, one of ordinary skill in the art should be able to readily determine whether a given crystalline form is the same crystalline form as described above and shown in FIG. 1.

In certain embodiments, the crystalline salt of Compound I is complexed with water in a molar ratio of 1:1 crystalline salt to water. In certain such embodiments, the crystal lattice does not comprise molecules of water.

In certain embodiments, the crystalline salt of Compound I is complexed with water in a molar ratio of 1:2 crystalline salt to water. In certain such embodiments, the crystal lattice does not comprise molecules of water.

In certain embodiments, the crystalline salt of Compound I is complexed with water in a molar ratio of 1:2.5 crystalline salt to water. In certain such embodiments, the crystal lattice does not comprise molecules of water.

Figure 2:
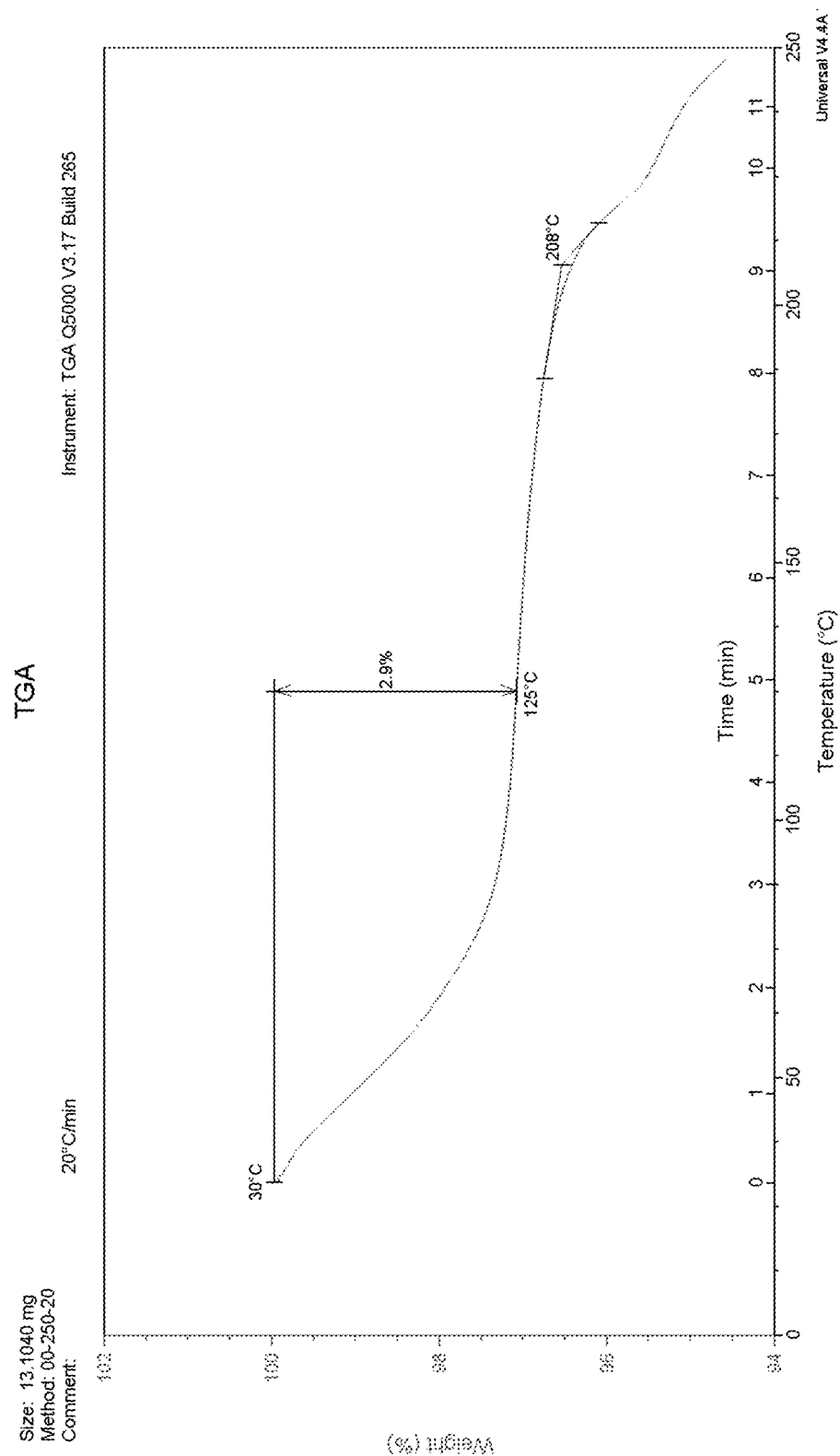
FIG. 2 is a spectrum showing a TG-IR analysis of Compound I•2(HCl).

In certain embodiments, the crystalline salt of Compound I has a thermogravimetric-infrared spectrum substantially similar to that shown in FIG. 2.

The term "substantially pure" as used herein, refers to a crystalline polymorph that is greater than 90% pure, meaning that it contains less than 10% of any other compound, including the corresponding amorphous compound or an alternative polymorph of the crystalline salt. Preferably, the crystalline polymorph is greater than 95% pure, or even greater than 98% pure.

In certain embodiments, the crystalline salt of Compound I has characteristic peaks in the XRPD pattern at values of two theta (0.2θ) as described herein above and is substantially pure. For example, the crystalline salt form can be at least 90% pure, preferably at least 95% pure, or more preferably at least 98% pure.

In certain embodiments, the crystalline salt of Compound I has an XRPD pattern that is substantially the same as that shown in FIG. 1 and is substantially pure. For example, the crystalline salt form can be at least 90% pure, preferably at least 95% pure, or more preferably at least 98% pure.

Methods of Making the Crystalline Salts

In certain embodiments, the invention relates to a method for the preparation of a crystalline salt of Compound I, comprising a) providing a freebase mixture of Compound I in a first organic solvent; b) combining the freebase mixture with a reagent solution comprising an acid and a second organic solvent under conditions sufficient to form a mixture comprising a salt of Compound I; and c) crystallizing the salt of Compound I from the mixture comprising a salt of Compound I.

In certain embodiments, the crystalline salt is a hydrochloride salt, e.g., a bis(hydrochloride) salt.

In certain embodiments, the first organic solvent comprises a polar aprotic solvent, such as acetonitrile, N,N-dimethylacetamide (DMA), dimethylformamide (DMF), dimethylsulfoxide (DMSO), diethyl ether, ethyl acetate, isopropyl acetate, methylethyl ketone, methyl tert-butyl ether (MTBE), N-methyl-2-pyrrolidone (NMP), tetrahydrofuran. Preferably, the polar aprotic solvent is methyl tert-butyl ether.

In certain embodiments, the first organic solvent further comprises a non-polar solvent. Non-polar solvents include, for example, benzene, heptaine, hexanes, and toluene. In certain embodiments, the non-polar solvent is toluene.

In certain embodiments, the acid is hydrochloric acid.

In certain embodiments, the second organic solvent is a polar protic solvent, such as ethanol, methanol, 2-propanol, 1-butanol, water, or any combination thereof. Preferably, the polar protic solvent is methanol.

In certain embodiments, the mixture comprising a salt of Compound I formed in step b) is a solution.

In certain embodiments, the mixture comprising the salt of Compound I is a solution, and the step of crystallizing the salt from the mixture comprises bringing the solution to supersaturation to cause Compound I to precipitate out of solution.

In certain embodiments, bringing the mixture comprising the salt of Compound I to supersaturation comprises the slow addition of an anti-solvent, such as heptanes, hexanes, ethanol, or another polar or non-polar liquid miscible with the organic solvent, allowing the solution to cool (with or without seeding the solution), reducing the volume of the solution, or any combination thereof. In certain embodiments, bringing the mixture comprising the salt of Compound I to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises inducing crystallization. The method can also comprise the step of drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.). In certain embodiments, inducing crystallization comprises seeding the solution with crystalline seeds of the salt of Compound I.

In certain embodiments, the preparation method further comprises isolating the salt crystals, e.g., by filtering the crystals, by decanting fluid from the crystals, or by any other suitable separation technique. In further embodiments, the preparation method further comprises washing the crystals.

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the salt crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene.

In certain embodiments, washing the crystals comprises washing the crystalline salt of Compound I with a solvent or a mixture of one or more solvents, which are described above. In certain embodiments, the solvent or mixture of solvents is cooled prior to washing.

In certain embodiments, the method further comprises drying the crystalline salt.

The crystalline salts described herein may be made according to the above-described method.

Pharmaceutical Compositions

The invention provides pharmaceutical compositions, each comprising one or more crystalline salts of the invention and a pharmaceutically acceptable carrier. In certain embodiments, the pharmaceutical composition comprises a crystalline salt of the invention and a pharmaceutically acceptable carrier. In certain embodiments, the pharmaceutical composition comprises a plurality of crystalline salts of the invention and a pharmaceutically acceptable carrier.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

In certain embodiments, a pharmaceutical composition of the invention further comprises at least one additional pharmaceutically active agent other than a compound of the invention. The at least one additional pharmaceutically active agent can be an agent useful in the treatment of a disease or condition characterized by aberrant plasma kallikrein activity. For example, the at least one additional pharmaceutically active agent can be an anticoagulation agent, an anti-platelet agent, or a thrombolytic agent.

Anticoagulation agents prevent the coagulation of blood components and thus prevent clot formation, for example in atrial fibrillation. Anticoagulants include, but are not limited to, heparin, warfarin, coumadin, dicumarol, phenprocoumon, acenocoumarol, ethyl biscoumacetate, hirudin, bivalarutin, direct thrombin inhibitors, and indandione derivatives.

Anti-platelet agents inhibit platelet aggregation and are often used to prevent thromboembolic stroke in patients who have experienced a transient ischemic attack, stroke, or atrial fibrillation. Anti-platelet agents include, but are not limited to, aspirin, thienopyridine derivatives such as ticlopodine and clopidogrel, dipyridamole, and sulfinpyrazone, as well as RGD mimetics.

Thrombolytic agents lyse clots that cause thromboembolic phenomena such as stroke, myocardial infarction, and pulmonary thromboembolism. Thrombolytic agents include, but are not limited to, plasminogen, a2-antiplasmin, streptokinase, antistreplase, TNK, tissue plasminogen activator (tPA), and urokinase. Tissue plasminogen activator includes native tPA and recombinant tPA, as well as modified forms of tPA that retain the enzymatic or fibrinolytic activities of native tPA.

Pharmaceutical compositions of the invention can be prepared by combining one or more crystalline salts of the invention with a pharmaceutically acceptable carrier and, optionally, one or more additional pharmaceutically active agents.

In certain embodiments, the invention provides a pharmaceutical composition that is formulated for the prophylactic or therapeutic treatment of a disease or condition characterized by aberrant plasma kallikrein activity.

Methods of Use

The present invention provides compounds that inhibit the formation of thrombin via the intrinsic pathway and thus reduce the risk of new pathogenic thrombus formation (vessel occlusion or reocclusion) and also improve fibrinolytic-induced reperfusion when given as adjunctive therapy with a fibrinolytic regimen. Diseases and conditions that can be treated using the compounds of the present invention include, but are not limited to, stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

For example, in patients with angioedema conditions, small polypeptide PK inhibitor DX-88 (ecallantide) alleviates edema in patients with hereditary angioedema (HAE). Williams, A. et al. (2003) *Transfus. Apher. Sci.* 29:255-8; Schneider, L. et al. (2007) *J Allergy Clin Immunol.* 120:416-22; and Levy, J. H. et al. (2006) *Expert Opin. Invest. Drugs* 15:1077-90. A bradykinin B2 receptor antagonist, Icatibant, is also effective in treating HAE. Bork, K. et al. (2007) *J. Allergy Clin. Immunol.* 119:1497-1503. Because plasma kallikrein generates bradykinin, inhibition of plasma kallikrein is expected to inhibit bradykinin production.

For example, in coagulation resulting from fibrinolytic treatment (e.g., treatment with tissue plasminogen activator or streptokinase), higher levels of plasma kallikrein are found in patients undergoing fibrinolysis. Hoffmeister, H. M. et al. (1998) *J. Cardiovasc. Pharmacol.* 31:764-72. Plasmin-mediated activation of the intrinsic pathway has been shown to occur in plasma and blood and was markedly attenuated in plasma from individuals deficient in any of the intrinsic pathway components. Ewald, G. A. et al. (1995) *Circulation* 91:28-36.

Individuals who have had an acute MI were found to have elevated levels of activated plasma kallikrein and thrombin. Hoffmeister, H. M., et al. (1998) *Circulation* 98:2527-33.

DX-88 reduced brain edema, infarct volume, and neurological deficits in an animal model of ischemic stroke. Storini, C. et al. (2006) *J. Pharm. Exp. Ther.* 318:849-854. C1-inhibitor reduced infarct size in a mouse model of middle cerebral artery occlusion (MCAO). De Simoni, M. G. et al. (2004) *Am. J. Pathol.* 164:1857-1863; and Akita, N. et al. (2003) *Neurosurgery* 52:395-400). B2 receptor antagonists were found to reduce the infarct volume, brain swelling, and neutrophil accumulation and were neuroprotective in an MCAO animal model. Zausinger, S. et al. (2003) *Acta Neurochir.* Suppl. 86:205-7; Lumenta, D. B. et al. (2006) *Brain Res.* 1069:227-34; Ding-Zhou, L. et al. (2003) *Br. J Pharmacol.* 139:1539-47.

Regarding blood loss during cardiopulmonary bypass (CPB), it has been found that the kallikrein-kinin (i.e., contact) system is activated during CABG. Wachtfogel, Y. T. (1989) *Blood* 73:468. Activation of the contact system during CPB results in up to a 20-fold increase in plasma bradykinin. Cugno, M. et al. (2006) Chest 120:1776-82; and Campbell, D. J. et al. (2001) *Am. J. Physiol. Reg. Integr. Comp. Physiol.* 281:1059-70.

Plasma kallikrein inhibitors P8720 and PKSI-527 have also been found to reduce joint swelling in rat models of arthritis. De La Cadena, R. A. et al. (1995) *FASEB J.* 9:446-52; Fujimori, Y. (1993) *Agents Action* 39:42-8. It has also been found that inflammation in animal models of arthritis was accompanied by activation of the contact system. Blais, C. Jr. et al. (1997) *Arthritis Rheum.* 40:1327-33.

Additionally, plasma kallikrein inhibitor P8720 has been found to reduce inflammation in an acute and chronic rat model of inflammatory bowel disease (IBD). Stadnicki, A. et al. (1998) *FASEB J.* 12:325-33; Stadnicki, A. et al. (1996) *Dig. Dis. Sci.* 41:912-20; and De La Cadena, R. A., et al. (1995) *FASEB J.* 9:446-52. The contact system is activated during acute and chronic intestinal inflammation. Sartor, R. B. et al. (1996) *Gastroenterology* 110:1467-81. It has been found that B2 receptor antagonist, an antibody to high molecular weight kininogen, or reduction in levels of kininogen reduced clinicopathology in animal models of IBD. Ibid.; Arai, Y. et al. (1999) *Dig. Dis. Sci.* 44:845-51; and Keith, J. C. et al. (2005) *Arthritis Res. Therapy* 7:R769-76.

H-D-Pro-Phe-Arg-chloromethylketone (CMK), an inhibitor of PK and FXII and a physiological inhibitor (C1-inhibitor), has been found to reduce vascular permeability in multiple organs and reduce lesions in lipopolysaccharide (LPS)- or bacterial-induced sepsis in animals. Liu, D. et al. (2005) *Blood* 105:2350-5; Persson, K. et al. (2000) *J. Exp. Med.* 192:1415-24. Clinical improvement was observed in sepsis patients treated with C1-inhibitor. Zeerleder, S. et al. (2003) *Clin. Diagnost. Lab. Immunol.* 10:529-35; Caliezi, C., et al. (2002) *Crit. Care Med.* 30:1722-8; and Marx, G. et al. (1999) *Intensive Care Med.* 25:1017-20. Fatal cases of septicemia are found to have a higher degree of contact activation. Martinez-Brotons, F. et al. (1987) *Thromb. Haemost.* 58:709-713; and Kalter, E. S. et al. (1985) *J. Infect. Dis.* 151:1019-27.

It has also been found that prePK levels are higher in diabetics, especially those with proliferative retinopathy, and correlate with fructosamine levels. Gao, B.-B., et al. (2007) *Nature Med.* 13:181-8; and Kedzierska, K. et al. (2005) *Archives Med. Res.* 36:539-43. PrePK is also found to be highest in those with a sensorimotor neuropathy. Christie, M. et al. (1984) *Thromb. Haemostas.* (Stuttgart) 52:221-3. PrePK levels are elevated in diabetics and are associated with increased blood pressure. PrePK levels independently correlate with the albumin excretion rate and are elevated in diabetics with macroalbuminuria, suggesting prePK may be a marker for progressive nephropathy. Jaffa, A. A. et al. (2003) *Diabetes* 52:1215-21. B1 receptor antagonists have been found to decrease plasma leakage in rats treated with streptozotocin. Lawson, S. R. et al. (2005) *Eur. J. Pharmacol.* 514:69-78. B1 receptor antagonists can also prevent streptozotocin-treated mice from developing hyperglycemia and renal dysfunction. Zuccollo, A. et al. (1996) *Can. J. Physiol. Pharmacol.* 74:586-9.

In certain aspects, the invention provides a crystalline salt of Compound I, for use as a medicament.

In certain aspects, the invention provides methods of treating or preventing a disease or condition characterized by aberrant plasma kallikrein activity. The method includes the step of administering to a subject in need thereof a therapeutically effective amount of a crystalline salt of Compound I, thereby treating or preventing the disease or condition characterized by aberrant plasma kallikrein activity. By reducing plasma kallikrein activity in the subject, the disease or condition characterized by aberrant plasma kallikrein activity is treated.

The terms "treat," "treating," and "treatment" as used herein means prevent, halt or slow the progression of, or eliminate a disease or condition in a subject. In some embodiments "treat," "treating," and "treatment" means halt or slow the progression of, or eliminate a disease or condition in a subject. In some embodiments, "treat," "treating," and "treatment" means reducing at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Alternatively, in certain aspects, the invention provides a crystalline salt of Compound I for treatment of a disease or condition characterized by aberrant plasma kallikrein activity.

Alternatively, in certain aspects, the invention provides the use of a crystalline salt of Compound I for the manufacture of a medicament for use in treatment of a disease or condition characterized by aberrant plasma kallikrein activity.

As used herein, a "disease or condition characterized by aberrant plasma kallikrein activity" refers to any disease or condition in which it is desirable to reduce plasma kallikrein activity. For example, it may be desirable to reduce plasma kallikrein activity in the setting of inappropriate activation or hyperactivation of kallikrein. As another example, it may be desirable to reduce plasma kallikrein activity in the setting of a hypercoagulable state. As another example, it may be desirable to reduce plasma kallikrein activity in the setting of tissue ischemia that is associated with the presence or formation of thrombus.

In certain embodiments, the disease or condition characterized by aberrant plasma kallikrein activity is selected from the group consisting of stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

In certain embodiments, the disease or condition characterized by aberrant plasma kallikrein activity is angioedema.

In certain embodiments, the disease or condition characterized by aberrant plasma kallikrein activity is acquired angioedema or hereditary angioedema (HAE).

Acquired Angioedema (AAE) (Caldwell J R, et al. Clin Immunol Immunopathol. 1972; 1:39-52) is characterized in several ways, including by acquired deficiency of C1 inhibitor (C1-INH), hyperactivation of the classical pathway of human complement and angioedema symptoms mediated by bradykinin released by inappropriate activation of the contact-kinin system. AAE may be present in two forms, AAE type 1 (which is normally associated with another disease) and AAE type II, which is normally associated with an autoimmune disease. AAE may be caused by a number of factors, including, but not limited to, autoimmune diseases (for example, the production of anti-C1INH antibodies) or by an acquired mutation in C1 INH. Furthermore, the crystalline salts of Compound I may be used to treat side effects of angiotensin converting enzyme (ACE) inhibitor treatments. ACE inhibitors block the major pathway for breakdown of bradykinin. Inhibiting kallikrein formation through the use of the crystalline salts of the invention reduces the formation of bradykinin.

In certain embodiments, the disease or condition characterized by aberrant plasma kallikrein activity is hereditary angioedema (HAE). In certain embodiments, the hereditary angioedema is Type I hereditary angioedema. Alternatively, the hereditary angioedema may be Type II hereditary angioedema. Alternatively, the hereditary angioedema may be Type III hereditary angioedema.

In certain embodiments, the crystalline salt of Compound I is used for prophylactic treatment of HAE. In other embodiments, the crystalline salt of Compound I is used for acute treatment of HAE.

In certain embodiments, the crystalline salt of Compound I is used for the prevention or treatment of angioedema attacks in a subject with HAE. In certain embodiments, the crystalline salt of Compound I is used as a preventive treatment to reduce the frequency of angioedema attacks in a subject with HAE. In other embodiments, the crystalline salt of Compound I is used for the treatment of an acute angioedema attack in a subject with HAE.

In certain embodiments, the disease or condition characterized by aberrant plasma kallikrein activity is stroke.

In certain embodiments, the disease or condition characterized by aberrant plasma kallikrein activity is reperfusion injury.

In certain embodiments, the disease or condition characterized by aberrant plasma kallikrein activity is acute myocardial infarction.

In certain embodiments, the disease or condition characterized by aberrant plasma kallikrein activity is hemorrhage.

In certain embodiments, the disease or condition characterized by aberrant plasma kallikrein activity is blood loss during cardiopulmonary bypass.

In certain embodiments, the disease or condition characterized by aberrant plasma kallikrein activity is selected from the group consisting of retinopathy, diabetic retinopathy, diabetic macular edema, diabetic macular degeneration, age-related macular edema, age-related macular degeneration, and proliferative retinopathy.

Formulations, Routes of Administration, and Dosing

The crystalline salts of Compound I described herein can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the crystalline salts of Compound I (also referred to herein as an "active compound") may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active compound which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active compound plus any additional desired ingredient present in the previously sterile-filtered solutions.

For topical administration, the crystalline salts of Compound I may be applied in pure form, i.e., when they are prepared in liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the crystalline salts of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the crystalline salts of the invention to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the crystalline salts of Compound I can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the crystalline salt of Compound I required for use in treatment will vary not only with the particular crystalline salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Crystalline salts of Compound I can be conveniently formulated in unit dosage form; for example, containing 5 to 1000 mg, 10 to 750 mg, 50 to 500 mg, 75 mg to 350 mg, 75 mg to 300 mg, 75 mg to 250 mg, 75 mg to 200 mg, 75 mg to 175 mg, 75 mg to 150 mg, 75 mg to 125 mg, 100 mg to 750 mg, 100 mg to 500 mg, 100 mg to 350 mg, 100 mg to 300 mg, 100 mg to 250 mg, 100 mg to 200 mg, 100 mg to 175 mg, 100 mg to 150 mg, 100 mg to 125 mg, 125 mg to 350 mg, 125 mg to 300 mg, 125 mg to 250 mg, 125 mg to 200 mg, 125 mg to 175 mg, 125 mg to 150 mg, including, for example, 5 mg, 10 mg, 25 mg, 50 mg, 75 mg, 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, and other such unit dosages falling within the foregoing unit dosage ranges, of active compound per unit dosage form. In one embodiment, the invention provides a composition comprising a crystalline salt of Compound I formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Crystalline salts of Compound I can also be administered in combination with other therapeutic agents, for example, other agents that are useful for treating or preventing ischemia, blood loss, or reperfusion injury.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active compound for at least 30 days, and preferably 60 days.

In certain embodiments, a crystalline salt of Compound I is formulated for intraocular administration, for example direct injection or insertion within or in association with an intraocular medical device.

The crystalline salts of Compound I may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver crystalline salts of the invention to the region of a body which has been treated by interventional technique.

In exemplary embodiments, a crystalline salt of Compound I may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the active compound is coated, adsorbed, placed, or otherwise incorporated into the device by methods known in the art. For example, the compound may be embedded and released from within ("matrix type") or surrounded by and released through ("reservoir type") polymer materials that coat or span the medical device. In the latter example, the compound may be entrapped within the polymer materials or coupled to the polymer materials using one or more the techniques for generating such materials known in the art. In other formulations, the compound may be linked to the surface of the medical device without the need for a coating, for example by means of detachable bonds, and release with time or can be removed by active mechanical or chemical processes. In other formulations, the compound may be in a permanently immobilized form that presents the compound at the implantation site.

In certain embodiments, the active compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/ PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D, L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/ PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the crystalline salt of Compound I is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the active compound is formulated for release from the polymer coating into the environment in which the medical device is placed. Preferably, the compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the active compound from the polymer coating can be controlled. For example, the diffusion coefficient of the one or more polymer coatings can be modulated to control the release of the compound from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the compound from the polymer coating). Yet another embodiment of the invention includes a device having a plurality of polymer coatings, each having a plurality of diffusion coefficients. In such embodiments of the invention, the release of the active compound from the polymer coating can be modulated by the plurality of polymer coatings.

In yet another embodiment of the invention, the release of the active compound from the polymer coating is controlled by modulating one or more of the properties of the polymer composition, such as the presence of one or more endogenous or exogenous compounds, or alternatively, the pH of the polymer composition. For example, certain polymer compositions can be designed to release a compound in response to a decrease in the pH of the polymer composition.

Kits

The invention also provides a kit, comprising a crystalline salt of Compound I, at least one other therapeutic agent, packaging material, and instructions for administering the crystalline salt of Compound I and the other therapeutic agent or agents to a mammal to treat or prevent a disease or condition characterized by aberrant kallikrein activity in the mammal. In one embodiment, the mammal is a human.

EXAMPLES

Materials and Methods
X-Ray Powder Diffraction

The XRPD pattern was collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Thermogravimetric Analysis

TG analyses were performed using a TA Instruments Discovery thermogravimetric analyzer with an IR furnace. Temperature calibration was performed using nickel and Alumel™. Each sample was placed in an aluminum pan. The sample was hermetically sealed, the lid pierced, then inserted into the TG furnace. The furnace was heated under nitrogen. The acquisition scan rate is recorded in the thermogram header, while the heating range can be determined from the individual plot.

Infrared (IR) Spectroscopy

Thermogravimetric infrared (TG-IR) analysis was performed on a TA Instruments Q5000 IR thermogravimetric (TG) analyzer interfaced to a Magna-IR 560® Fourier transform infrared (FT-IR) spectrophotometer (Thermo Nicolet) equipped with an Ever-Glo mid/far IR source, a potassium bromide (KBr) beamsplitter, and a mercury cadmium telluride (MCT-A) detector. The FT-IR wavelength verification was performed using polystyrene, and the TG calibration standards were nickel and Alumel™. The sample was placed in a platinum sample pan, and the pan was inserted into the TG furnace. The TG instrument was started first, immediately followed by the FT-IR instrument. The TG instrument was operated under a flow of helium at 90 and 10 cc/min for the purge and balance, respectively. The furnace was heated under helium at a rate of 20° C./minute to a final temperature of 350° C. IR spectra were collected approximately every 16 seconds for approximately 13 minutes. Each IR spectrum represents 16 co-added scans collected at a spectral resolution of 4 cm$^{-1}$. Volatiles were identified from a search of the High Resolution Nicolet Vapor Phase spectral library.

Example 1: Synthetic Protocol for Racemic Compound 54e

Reproduced from WO 2015/134998 and U.S. Patent Application Publication No. 2017/0073314 A1 (both incorporated by reference)

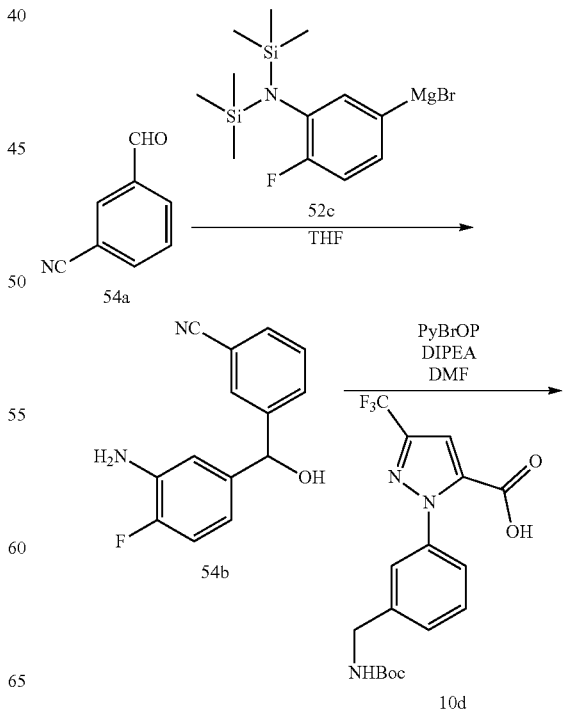

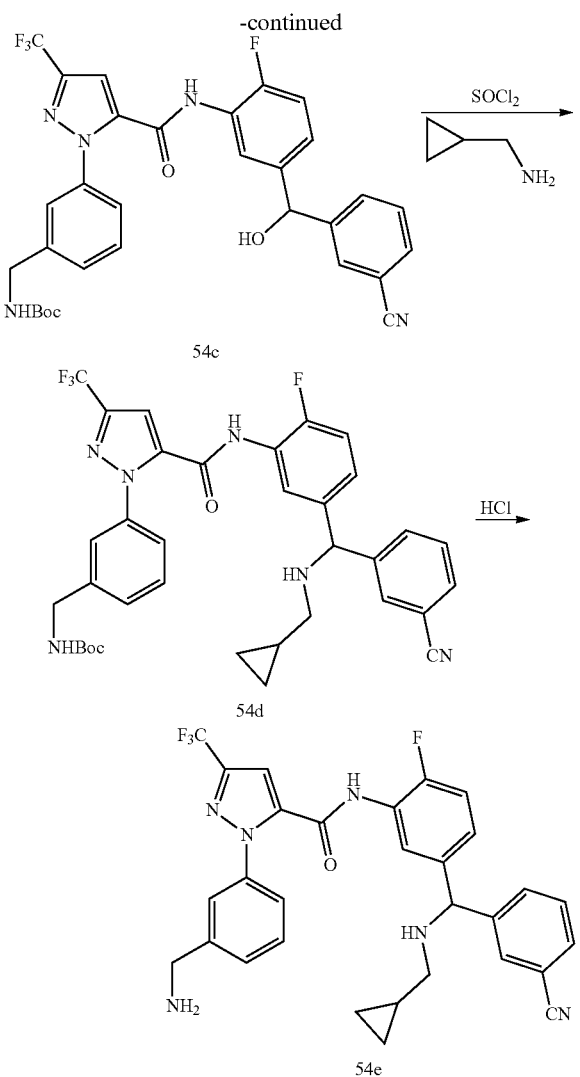

Preparation of 1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (54e)

Step-1: Preparation of 3-((3-amino-4-fluorophenyl)(hydroxy)methyl)benzonitrile (54b)

To a solution of 3-formylbenzonitrile (54a) (29 g, 217 mmol) in tetrahydrofuran (200 mL) cooled to 0° C. was added freshly prepared Grignard reagent (52c) (245 mL, 221 mmol, 0.9 M in THF) stirred at 0° C. for 1 h, and room temperature for 18 h. The reaction mixture was quenched with 1 N HCl (aq. 440 mL), stirred for 3 h, neutralized with NaOH (2 N, aq.) to pH=~8. The reaction mixture was extracted with ethyl acetate (600, 300 mL). The combined extracts were washed with brine (120 mL), dried over MgSO$_4$, filtered and concentrated in vacuum. The crude product was purified by flash column chromatography [silica gel, eluting with hexanes/ethyl acetate (1:0 to 1:1) to give 3-((3-amino-4-fluorophenyl)(hydroxy)methyl)benzonitrile (54b) (36.28 g) as a brown gum which was used as such for next step; MS (ES+) 265.3 (M+23).

Step-2: Preparation of tert-butyl 3-(5-(5-((3-cyanophenyl)(hydroxy)methyl)-2-fluorophenylcarbamoyl)-3-(trifluoromethyl)-1H-pyrazol-1-yl)benzylcarbamate (54c)

To a solution of 3-((3-amino-4-fluorophenyl)(hydroxy)methyl)benzonitrile (54b) (24.682 g, 102 mmol) in DMF (480 mL) was added 1-(3-(((tert-butoxycarbonylamino)methyl)phenyl)-3-(trifluoromethyl)-1H-pyrazole-5-carboxylic acid (10d) (35.0 g, 91 mmol), N-ethyl-N-isopropylpropan-2-amine (132 mL, 758 mmol), bromotripyrrolidin-1-ylphosphonium hexafluorophosphate (V) (PyBrOP, 42.8 g, 91 mmol) and stirred at room temperature for 19 h. The reaction mixture was diluted with ethyl acetate (1000 mL), washed with water (500, 400 mL), brine (400 mL), dried over MgSO$_4$, filtered and concentrated in vacuum. The crude product was purified by flash column chromatography [silica gel, eluting with hexanes/ethyl acetate (1:0 to 1:1)] to afford tert-butyl 3-(5-(5-((3-cyanophenyl)(hydroxy)methyl)-2-fluorophenylcarbamoyl)-3-(trifluoromethyl)-1H-pyrazol-1-yl)benzylcarbamate (54c) (4.583 g, 5% for two steps) as a yellow solid; $^1$H NMR (300 MHz, DMSO-d$_6$) δ 10.57 (s, 1H), 7.81 (t, J=1.7 Hz, 1H), 7.73-7.66 (m, 2H), 7.64-7.19 (m, 10H), 6.25 (d, J=4.0 Hz, 1H), 5.78 (d, J=4.0 Hz, 1H), 4.19 (d, J=6.1 Hz, 2H), 1.37 (s, 9H); $^{19}$F NMR (282 MHz, DMSO-d$_6$) δ −60.81, −123.09; MS (ES+) 632.3 (M+23).

Step-3: Preparation of tert-butyl 3-(5-(5-((3-cyanophenyl)(cyclopropylmethylamino)methyl)-2-fluorophenylcarbamoyl)-3-(trifluoromethyl)-1H-pyrazol-1-yl)benzylcarbamate (54d)

To a solution of tert-butyl 3-(5-(5-((3-cyanophenyl)(hydroxy)methyl)-2-fluorophenylcarbamoyl)-3-(trifluoromethyl)-1H-pyrazol-1-yl)benzylcarbamate (54c) (1.333 g, 2.187 mmol) in dichloromethane (40 mL) at 0° C. was added thionyl chloride (0.340 mL, 4.59 mmol) and warmed to room temperature over 2 h. The reaction mixture was quenched with triethyl amine (2.0 mL, 14.35 mmol) stirred at room temperature for 1 h. It was then treated with cyclopropylmethanamine (4.30 mL, 48.0 mmol), concentrated to remove most of dichloromethane followed by addition of acetonitrile (30 mL), stirring at 70° C. for 14 h, and concentration in vacuum to dryness. The residue was treated with chlorofrom (200 mL), washed with water (100 mL), dried over MgSO$_4$ followed by filtration and concentration. The crude product was purified by flash column chromatography [silica gel eluting with hexanes/ethyl acetate (1:0 to 2:1)] to afford tert-butyl 345454(3-cyanophenyl)(cyclopropylmethylamino)methyl)-2-fluorophenylcarbamoyl)-3-(trifluoromethyl)-1H-pyrazol-1-yl)benzylcarbamate (54d) (184 mg, 13%) as colorless gum; $^1$H NMR (300 MHz, DMSO-d$_6$) δ 10.56 (s, 1H), 7.89 (t, J=1.7 Hz, 1H), 7.77-7.71 (m, 1H), 7.70-7.30 (m, 10H), 7.22 (dd, J=10.3, 8.5 Hz, 1H), 4.93 (s, 1H), 4.19 (d, J=6.2 Hz, 2H), 2.26 (d, J=6.6 Hz, 2H), 1.37 (s, 9H), 1.00-0.80 (m, 1H), 0.45-0.28 (m, 2H), 0.12-0.01 (m, 2H); $^{19}$F NMR (282 MHz, DMSO-d$_6$) δ −60.80, −123.20; MS (ES+) 663.4 (M+1).

Step-4: Preparation of 1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (54e)

To a solution of tert-butyl 3-(5-(5-((3-cyanophenyl)(cyclopropylmethylamino)methyl)-2-fluorophenylcarbamoyl)-

3-(trifluoromethyl)-1H-pyrazol-1-yl)benzylcarbamate (54d) (161 mg, 0.243 mmol) in 1,4-Dioxane (18 mL) was added hydrogen chloride (2.60 mL, 10.40 mmol, 4 M in 1,4-dioxane) and stirred at room temperature for 16 h. the reaction mixture was treated with hexanes, decanted, washed with hexanes, and decanted again. The insoluble crude product was purified by flash column chromatography [silica gel, eluting with chloroform/CMA80 (1:0 to 2:1)] to afford 1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (54e). The pure product was dissolved in methanol (10 mL) and added 4 N HCl (aq. 0.14 mL) followed by concentration in vacuum to dryness to give HCl salt of 1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (54e) (74 mg, 48%) white solid; $^1$H NMR (300 MHz, DMSO-d6, D2O ex NMR) δ 8.13 (t, J=1.7 Hz, 1H), 7.98-7.84 (m, 3H), 7.73-7.64 (m, 3H), 7.63-7.48 (m, 4H), 7.44 (dd, J=10.2, 8.6 Hz, 1H), 5.75 (s, 1H), 4.12 (s, 2H), 2.76 (d, J=7.2 Hz, 2H), 1.17-0.94 (m, 1H), 0.68-0.47 (m, 2H), 0.34-0.24 (m, 2H); $^{19}$F NMR (282 MHz, DMSO-d6) δ −60.82, −120.02; MS (ES+): 563.3 (M+1); Analysis calculated for $C_{30}H_{26}F_4N_6O \cdot 2.0$ HCl$\cdot 3.0$ H$_2$O: C, 52.26; H, 4.97; N, 12.19. Found: C, 52.26; H, 5.00; N, 11.72.

Example 2: Separation of Enantiomers of Racemic Compound 54e

Reproduced from WO 2015/134998 and U.S. Patent Application Publication No. 2017/0073314 A1 (both incorporated by reference)

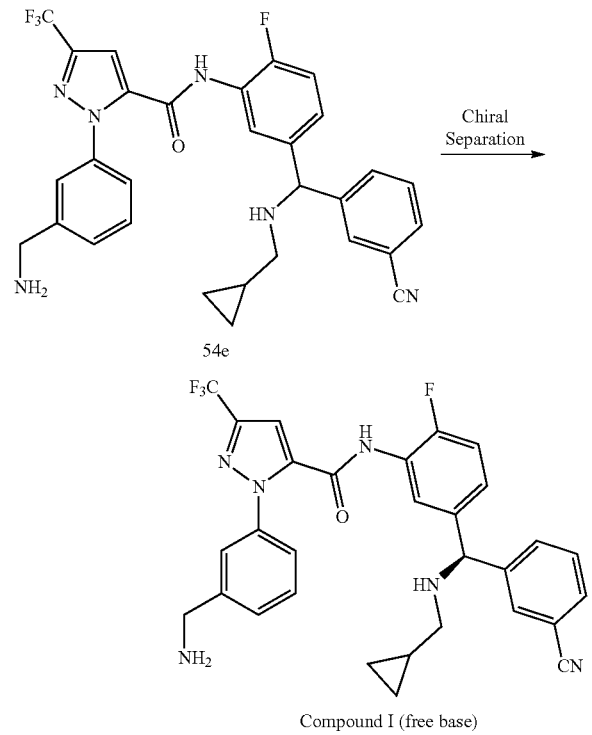 [SMILES: N#Cc1cccc(C(NCC2CC2)c2ccc(F)c(NC(=O)c3cc(C(F)(F)F)nn3-c3cccc(CN)c3)c2)c1 ; N#Cc1cccc([C@@H](NCC2CC2)c2ccc(F)c(NC(=O)c3cc(C(F)(F)F)nn3-c3cccc(CN)c3)c2)c1]

Separation of (+)-1-(3-(aminomethyl)phenyl)-N-(5-((3-cyanophenyl)(cyclopropyl-methylamino) methyl)-2-fluorophenyl)-3-(trifluoromethyl)-1H-pyrazole-5-carboxamide (Compound I), and (−)-1-(3-(aminomethyl)phenyl)-N-(5-(3-cyanophenyl)(cyclopropyl-methylamino)methyl)-2-fluorophenyl)-3-(trifluoromethyl)-1H-pyrazole-5-carboxamide ((−)-enantiomer)

Isomers of Racemic 1-(3-(aminomethyl)phenyl)-N-(5-(3-cyanophenyl)(cyclopropyl-methylamino)methyl)-2-fluorophenyl)-3-(trifluoromethyl)-1H-pyrazole-5-carboxamide (54e) (0.4 g) were separated by using preparative SFC method using the following conditions to furnish:

| Preparative SFC Method used: | |
| --- | --- |
| Column | 20 mm × 25.0 cm ChromegaChiral CCS from Regis Technologies (Morton Grove, IL) |
| CO$_2$ Co-solvent (Solvent B) | Methanol: Isopropanol (1:1) with 1% Isopropylamine |
| Isocratic Method | 20% Co-solvent at 80 mL/min |
| System Pressure | 200 bar |
| Column Temperature | 25° C. |
| Sample Diluent | Methanol: Isopropanol |
| Chiral Purity of peaks was determined by following Analytical SFC Method: | |
| Column | 4.6 × 100 mm ChiralPak AS from Chiral Technologies (West Chester, PA) |
| CO$_2$ Co-solvent (Solvent B) | Methanol: Isopropanol (1:1) with 0.1% Isopropylamine |
| Isocratic Method | 5-65% Co-solvent Gradient at 4 mL/min |
| System Pressure | 100 bar |
| Column Temperature | 25° C. |
| Sample Diluent | Methanol |
| Peak-1 (Compound I) | 2.1 min 144 mg >95% ee (UV 254) 98.6% purity (UV 254) |
| Peak-2 ((−)-enantiomer) | 2.4 min 172 mg 95.5% ee (UV 254) 96.5% purity (UV 254) |

1. Peak-1 assigned as (+)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (Compound I) (144 mg, >95% ee) free base as white solid; Optical rotation: [α]$_D$=(+) 6.83 [CH$_3$OH, 1.2]; $^1$H NMR (300 MHz, DMSO-d$_6$) δ 10.53 (s, 1H, D$_2$O exchangeable), 7.88 (t, J=1.7 Hz, 1H), 7.77-7.71 (m, 1H), 7.67 (dt, J=7.7, 1.4 Hz, 1H), 7.63 (dd, J=7.5, 2.1 Hz, 1H), 7.56 (s, 1H), 7.54-7.47 (m, 2H), 7.47-7.38 (m, 2H), 7.34 (ddt, J=8.6, 5.9, 2.8 Hz, 2H), 7.22 (dd, J=10.3, 8.5 Hz, 1H), 4.93 (s, 1H), 3.77 (s, 2H), 2.31-2.21 (m, 2H), 0.97-0.80 (m, 1H), 0.42-0.33 (m, 2H), 0.10-0.02 (m, 2H); $^{19}$F NMR (282 MHz, DMSO-d$_6$) δ −60.73, −123.20; MS (ES+) 563.3 (M+1), 561.3 (M−1). To a solution of free base mixture of (+)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (Compound I) (120 mg) in methanol (15 mL) was added hydrogen chloride (0.969 mL, 1.938 mmol), stirred at room temperature for 10 min, evaporated to dryness to afford (+)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (Compound I) (100 mg) hydrochloride salt as white solid; $^1$H NMR (300 MHz, DMSO-d$_6$) δ 10.84 (s, 1H, D$_2$O exchangeable), 10.44 (s, 2H, D$_2$O exchangeable), 8.44 (s, 3H, D$_2$O exchangeable), 8.30 (s, 1H, D$_2$O exchangeable), 8.09 (d, J=7.9 Hz, 1H), 7.99 (d, J=6.8 Hz, 1H), 7.91-7.83 (m, 1H), 7.80-7.50 (m, 7H), 7.42 (dd, J=10.3, 8.6 Hz, 1H), 5.78 (d, J=6.9 Hz, 1H), 4.13 (d, J=5.7 Hz, 2H), 2.88-2.62 (m, 2H), 1.42-0.99 (m, 1H), 0.73-0.46 (m, 2H), 0.32 (d, J=4.4 Hz, 2H); $^{19}$F NMR (282 MHz, DMSO-d$_6$) δ −60.81, −119.99; MS (ES$^+$): MS (ES+) 563.3 (M+1), MS (ES−) 561.3 (M−1), 597.3 (M+Cl); Analysis calculated for C$_{30}$H$_{26}$F$_4$N$_6$O.2HCl.1.75H$_2$O: C, 54.02; H, 4.76; Cl, 10.63; N, 12.60. Found: C, 54.12; H, 4.83; Cl, 10.10; N, 11.97.

2. Peak-2 assigned as (−)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide ((−)-enantiomer) (172 mg, 95.5% ee) as free base was repurified by flash column chromatography (silica gel 12 g, eluting 0-30% MeOH in chloroform for 15 min) to afford (−)-1-(3-(aminomethyl)phenyl)-N-(5-(3-cyanophenyl)(cyclopropyl-methylamino)methyl)-2-fluorophenyl)-3-(trifluoromethyl)-1H-pyrazole-5-carboxamide ((−)-enantiomer) free base as an off-white solid; Optical rotation: [α]$_D$=(−) 5.44 [CH$_3$OH, 1.25]; $^1$H NMR (300 MHz, DMSO-d$_6$) δ 7.88 (t, J=1.6 Hz, 1H), 7.74 (d, J=8.1 Hz, 1H), 7.70-7.61 (m, 2H), 7.57 (s, 1H), 7.54-7.47 (m, 2H), 7.45-7.41 (m, 2H), 7.34 (ddq, J=8.7, 6.1, 3.5, 2.8 Hz, 2H), 7.22 (dd, J=10.3, 8.5 Hz, 1H), 4.93 (s, 1H), 3.78 (s, 2H), 2.25 (d, J=6.9 Hz, 2H), 0.90 (ddd, J=9.8, 8.0, 5.2 Hz, 1H), 0.47-0.29 (m, 2H), 0.04 (dd, J=5.0, 1.5 Hz, 2H); $^{19}$F NMR (282 MHz, DMSO-d$_6$) δ −60.73, −123.19; MS (ES+) 563.3 (M+1), MS (ES−), 561.3 (M−1). To a solution of free base of (−)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide ((−)-enantiomer) (0.124 g, 0.220 mmol) in methanol (15 mL) was added hydrogen chloride (1.102 mL, 2.204 mmol), stirred at room temperature for 10 min, evaporated to dryness to afford (−)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide ((−)-enantiomer) (0.121 g) hydrochloride salt as an off-white solid; $^1$H NMR: $^1$H NMR (300 MHz, DMSO-d$_6$) δ 10.82 (s, 1H, D$_2$O exchangeable), 10.36 (s, 2H, D$_2$O exchangeable), 8.38 (s, 3H, D$_2$O exchangeable), 8.27 (s, 1H), 8.06 (d, J=7.9 Hz, 1H), 7.98 (d, J=6.7 Hz, 1H), 7.87 (d, J=7.7 Hz, 1H), 7.78-7.49 (m, 7H), 7.48-7.37 (m, 1H), 5.78 (s, 1H), 4.13 (d, J=5.7 Hz, 2H), 2.72 (s, 2H), 1.14 (s, 1H), 0.56 (d, J=7.7 Hz, 2H), 0.31 (d, J=5.0 Hz, 2H); $^{19}$F NMR (282 MHz, DMSO-d$_6$) δ −60.82, −120.03; MS (ES$^+$): MS (ES+) 563.3 (M+1), MS (ES−) 561.3 (M−1), 597.2 (M+Cl); Analysis calculated for C$_{30}$H$_{26}$F$_4$N$_6$O.2HCl.1.75H$_2$O: C, 54.02; H, 4.76; Cl, 10.63; N, 12.60. Found: C, 54.12; H, 4.83; Cl, 10.10; N, 11.97.

Example 3: Preparation of a Seed Crystal of Compound I•2(HCl)

A solution of Compound I (see Example 2) in methyl tert-butyl ether (MTBE) (1 equiv) is added to a solution of HCl (aq) (2 equiv) in methanol (cold), followed by heating to about 30° C., and keeping it at about 30° C. for not longer than 5 hours while stirring at about 115 rpm. Compound I bis(HCl) is collected by filtration and dried. The crystalline material obtained can be used as a seed for the crystallization protocol described in Example 4.

Example 4: Large-Scale Synthetic & Crystallization Protocol for Compound I•2(HCl)

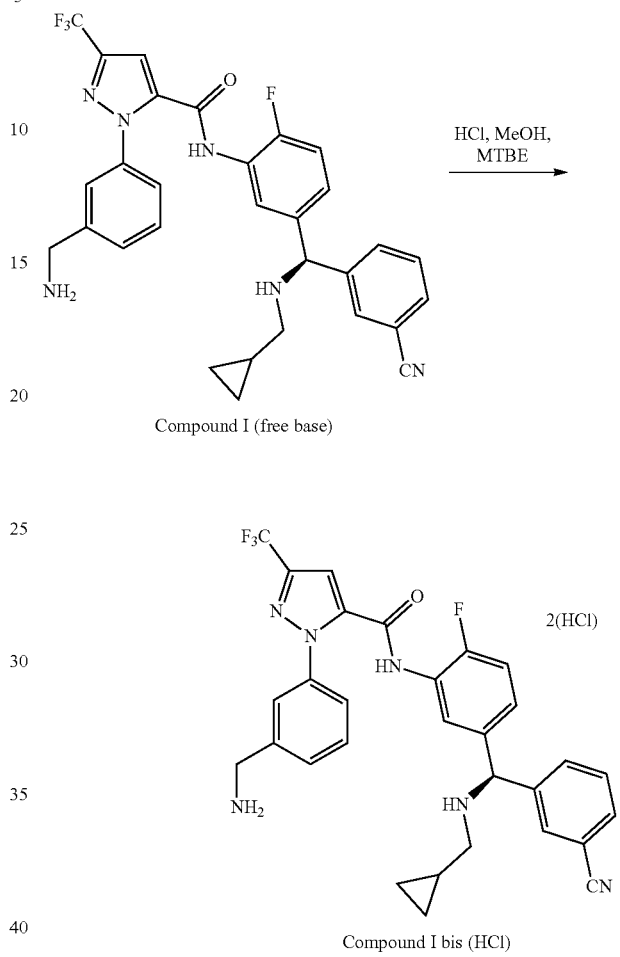

37% Aqueous hydrochloric acid (38.1 kg, 32.3 L, 2.14 equiv.) was charged to a clean and empty crystallization vessel, methanol (228.9 kg, 39.5 equiv.) was added, and the contents were cooled to −7±3° C. A solution of Compound I free base (approx. 101.8 kg; 180.9 moles) in MTBE (approx. 1,300 L) was filtered through a polish filter into the crystallization vessel at temperature −5±5° C. After rinse with MTBE, pre-weighed Compound I•2(HCl) seed crystals (1.39 kg, 0.012 equiv.; Example 3) were charged to the crystallization vessel via the manhole. The vessel content was heated to 30-33° C., and the agitation speed was set to 25-50 rpm. After confirmed crystallization, the slurry was agitated for another three to four hours. The product slurry was transferred to centrifuge and isolated by centrifugation. The product was washed with MTBE (585 L). After dry spinning the wet product, Compound I•2(HCl), it was discharged from the centrifuge, and the product was dried at ≤40° C. under vacuum in a cone drier. Product Compound I•2(HCl) yield: 100 kg; 157.4 mol; approx. 85%.

$^1$H NMR (300 MHz, DMSO-d$_6$) data is shown in the following table:

| Structure | Chemical Shift (ppm) | Class | Number of Hydrogens |
|---|---|---|---|
| (structure shown: F₃C-pyrazole-carboxamide with 2HCl, H₂N, cyclopropylmethyl, CN) | 0.02-0.10 | m | 2 |
| | 0.33-0.42 | m | 2 |
| | 0.80-0.97 | m | 1 |
| | 2.21-2.31 | m | 2 |
| | 3.77 | s | 2 |
| | 4.93 | s | 1 |
| | 7.22 | dd | 1 |
| | 7.34 | ddt | 2 |
| | 7.38-7.47 | m | 2 |
| | 7.47-7.54 | m | 2 |
| | 7.56 | s | 1 |
| | 7.63 | dd | 1 |
| | 7.67 | dt | 1 |
| | 7.71-7.77 | m | 1 |
| | 7.88 | t | 1 |
| | 10.53 | s | 1 |

$^{19}$F NMR (282 MHz, DMSO-$d_6$) data is shown in the following table:

| Structure | Fluorine Chemical Shifts (ppm) |
|---|---|
| (structure shown with 2HCl) | −60.81, −119.99 |

Compound I has two basic sites. The conjugate acid of the primary amine was calculated to have a pKa value of 8.89, and the conjugate acid of the secondary amine was calculated to have a pKa value of 7.86.

The XRPD pattern of Compound I•2(HCl) is shown in FIG. 1. Compound I•2(HCl) has characteristic peaks in its XRPD pattern at values of two theta (0.20) of 5.28, 8.96, 14.27, 16.18, 19.79, 21.16, 22.01, 23.31, 24.64, and 30.31.

TG-IR analysis indicated two, distinct weight loss regions: the first was completed by 125° C. while the second began at approximately 208° C. IR analysis of the off gasses from this experiment detected only trace amounts of water at the initial weight loss while HCl gas was detected at the 208° C. event. No other solvents were detected in the sample. Thus, it was determined that Compound I•2(HCl) initially loses water when heated and, when heated to above 200° C., the salt begins to break apart and HCl gas is evolved. The IR signal for all these events is very weak indicating that they are occurring over a range and not at a specified temperature. An exemplary TG-IR spectrum is shown in FIG. 2.

Example 5: Compound Assays

Compound I was assayed in an in vitro biochemical assay measuring inhibition of human plasma kallikrein activity. Experimental protocols and results of the assays are found in WO 2015/134998 and U.S. Patent Application Publication No. 2017/0073314 A1 (both incorporated by reference).

Results of this biochemical assay demonstrate that Compound I is a potent inhibitor of human plasma kallikrein activity.

Example 6: Pharmacokinetics of Compound I•2(HCl) in Healthy Subjects

As part of a Phase I, double-blind, placebo-controlled dose-ranging study, the pharmacokinetics of multiple ascending oral doses of Compound I•2(HCl) were evaluated in healthy subjects. Four ascending dose cohorts were enrolled for dosing in a sequential manner. At the start, twelve subjects were randomized into each cohort for administration of a 7-day or 14-day course of study drug (n=10/cohort received Compound I•2(HCl) and n=2/cohort received matching placebo) according to the following dose regimens: 125 mg Compound I•2(HCl) or placebo once per day (QD) for 7 days in Cohort 1; 250 mg Compound I•2(HCl) or placebo QD for 7 days in Cohort 2; 500 mg Compound I•2(HCl) or placebo QD for 7 days in Cohort 3; or 350 mg Compound I•2(HCl) or placebo QD for 14 days in Cohort 4. Overall, 37 out of the 40 subjects receiving multiple doses of Compound I•2(HCl) completed their respective dose regimens and were available for assessment of PK parameters at either Day 7 or Day 14.

Serial blood samples were drawn for pharmacokinetic analysis before dose administration on Day 7 or Day 14, and over the following 24 hours. The plasma samples for determination of Compound I•2(HCl) concentrations were analyzed with the use of a validated LC-MS/MS (Liquid Chromatography with tandem mass spectrometry) bioanalytical assay.

Figure 3:
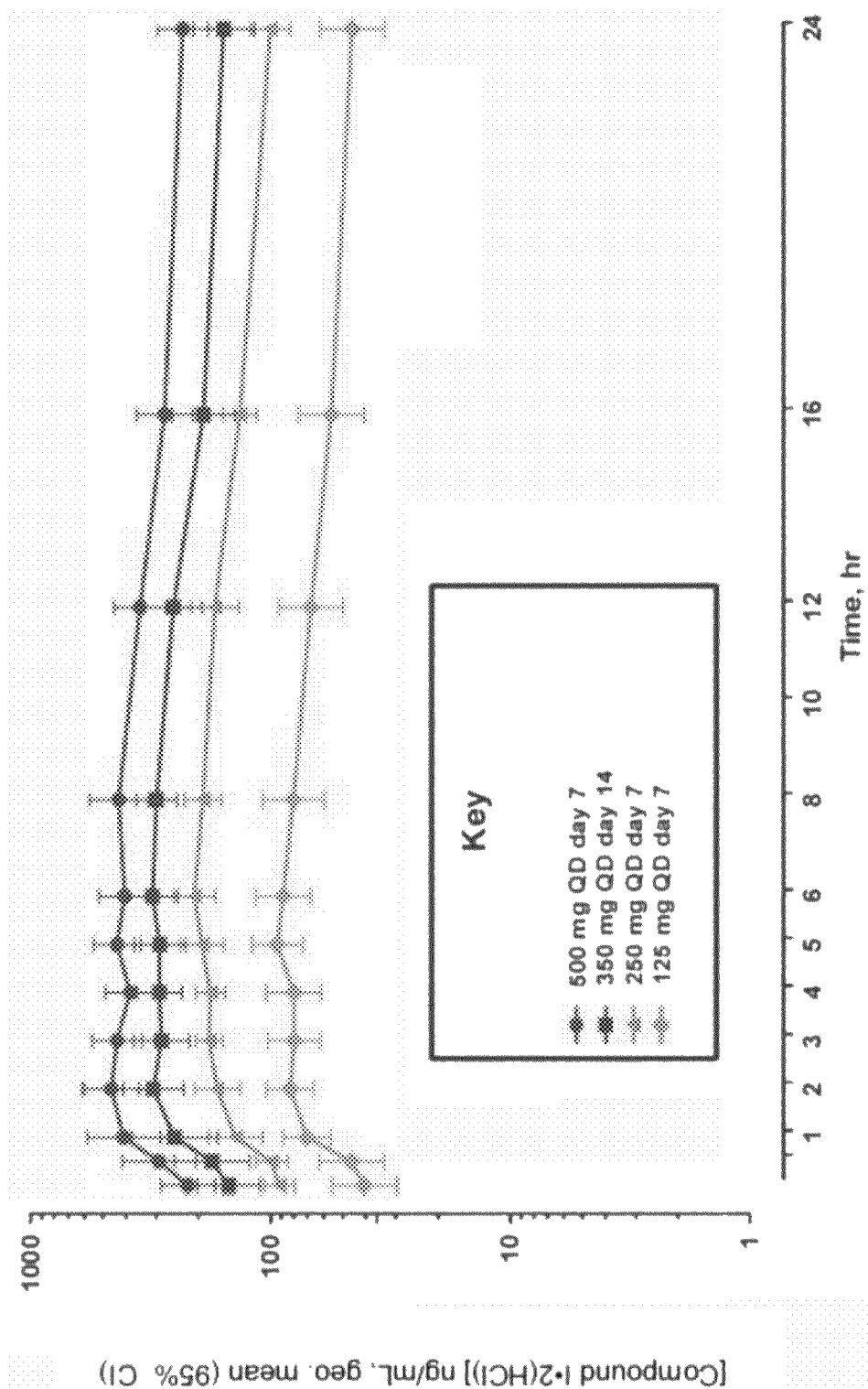
FIG. 3 shows plasma concentration of Compound I•2 (HCl) versus time profiles on Day 7 after once per day (QD) oral administration of Compound I•2(HCl) at 125, 250, and 500 mg QD; and on Day 14 after QD oral administration of Compound I•2(HCl) at 350 mg QD.

Plasma Compound I•2(HCl) concentration versus time profiles on Day 7 after QD oral administration of Compound I•2(HCl) at 125, 250, and 500 mg QD, and on Day 14 after QD oral administration of Compound I•2(HCl) at 350 mg QD, are shown in FIG. 3.

Table 1 provides a summary of plasma pharmacokinetic parameters [the maximum (peak) plasma drug concentration ($C_{max}$), time (observed time point) to reach maximum (peak) plasma drug concentration following drug administration ($T_{max}$), the observed trough plasma concentration at the end of the dosing interval (Ctau), and the area under the plasma concentration-time curve over the dosing interval (AUC$_{tau}$)] following 7 or 14 days of multiple oral doses of Compound I•2(HCl).

TABLE 1

Summary of plasma pharmacokinetic parameters following 7 or 14 days of multiple oral doses of Compound I•2(HCl) in healthy subjects (Day 7 or Day 14).

| Pharmacokinetic Parameter | Compound I•2(HCl) | | | |
|---|---|---|---|---|
| | 125 mg QD Day 7 (N = 10) | 250 mg QD Day 7 (N = 9) | 500 mg QD Day 7 (N = 9) | 350 mg QD Day 14 (N = 9) |
| $C_{max}$ (ng/mL)$^a$ | 97.8 | 217 | 517 | 363 |
| | (35) | (25) | (37) | (37) |
| $T_{max}$ (hr)$^b$ | 5.0 | 6.0 | 2.0 | 4.0 |
| | (2.0, 8.1) | (3.0, 12.0) | (1.0, 8.1) | (1.0, 8.0) |
| $C_{tau}$ (ng/mL)$^a$ | 46.1 | 101 | 235 | 158 |
| | (46) | (25) | (32) | (40) |

TABLE 1-continued

Summary of plasma pharmacokinetic parameters following 7 or 14 days of multiple oral doses of Compound I•2(HCl) in healthy subjects (Day 7 or Day 14).

| Pharmacokinetic Parameter | Compound I•2(HCl) | | | |
| --- | --- | --- | --- | --- |
| | 125 mg QD Day 7 (N = 10) | 250 mg QD Day 7 (N = 9) | 500 mg QD Day 7 (N = 9) | 350 mg QD Day 14 (N = 9) |
| $AUC_{tau}$ (ng · hr/mL)$^a$ | 1600 (41) | 3710 (23) | 8230 (34) | 5720 (34) |

$^a$ Data reported as geometric mean (CV % of geometric mean).
$^b$ $T_{max}$ reported as median (min, max).

Maximal plasma Compound I•2(HCl) concentrations were achieved at approximately 2 to 6 hours post-dose. An increase in dosage from 125 mg to 250 mg QD and 250 mg to 500 mg QD imparted reasonable dose proportionality. Across the full 4-fold dose range, exposure increased in a slightly greater than dose proportional manner with a 5.1- and 5.3-fold increase in geometric mean values of $AUC_{tau}$ and $C_{max}$, respectively.

INCORPORATION BY REFERENCE

All U.S. patents and U.S. and PCT published patent applications mentioned herein are hereby incorporated by reference in their entirety as if each individual patent or published application was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A crystalline salt of Compound I,

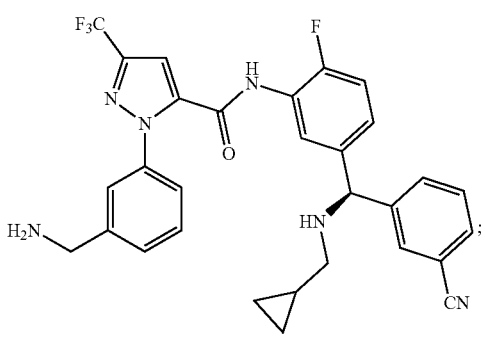

wherein the salt is a bis(hydrochloride) salt.

2. The crystalline salt of claim 1, having characteristic peaks in the X-ray powder diffraction (XRPD) pattern at values of two theta (° 2θ±0.2°) of 5.3, 9.0, and 22.0.

3. The crystalline salt of claim 1, having characteristic peaks in the X-ray powder diffraction (XRPD) pattern at values of two theta (° 2θ) of 5.3, 9.0, and 22.0.

4. The crystalline salt of claim 2, having characteristic peaks in the X-ray powder diffraction (XRPD) pattern at values of two theta (° 2θ±0.2°) of 5.3, 9.0, 19.8, 21.2, 22.0, and 23.3.

5. The crystalline salt of claim 3, having characteristic peaks in the X-ray powder diffraction (XRPD) pattern at values of two theta (° 2θ) of 5.3, 9.0, 19.8, 21.2, 22.0, and 23.3.

6. The crystalline salt of claim 4, having characteristic peaks in the X-ray powder diffraction (XRPD) pattern at values of two theta (° 2θ±0.2°) of 5.3, 9.0, 14.3, 16.2, 19.8, 21.2, 22.0, 23.3, 24.6, and 30.3.

7. The crystalline salt of claim 5, having characteristic peaks in the X-ray powder diffraction (XRPD) pattern at values of two theta (° 2θ) of 5.3, 9.0, 14.3, 16.2, 19.8, 21.2, 22.0, 23.3, 24.6, and 30.3.

8. The crystalline salt of claim 1, having characteristic peaks in the X-ray powder diffraction (XRPD) pattern at values of two theta (° 2θ±0.2°) of 5.28, 8.96, and 22.01.

9. The crystalline salt of claim 1, having characteristic peaks in the X-ray powder diffraction (XRPD) pattern at values of two theta (° 2θ) of 5.28, 8.96, and 22.01.

10. The crystalline salt of claim 8, having characteristic peaks in the X-ray powder diffraction (XRPD) pattern at values of two theta (° 2θ±0.2°) of 5.28, 8.96, 19.79, 21.16, 22.01, and 23.31.

11. The crystalline salt of claim 9, having characteristic peaks in the X-ray powder diffraction (XRPD) pattern at values of two theta (° 2θ) of 5.28, 8.96, 19.79, 21.16, 22.01, and 23.31.

12. The crystalline salt of claim 10, having characteristic peaks in the X-ray powder diffraction (XRPD) pattern at values of two theta (° 2θ±0.2°) of 5.28, 8.96, 14.27, 16.18, 19.79, 21.16, 22.01, 23.31, 24.64, and 30.31.

13. The crystalline salt of claim 11, having characteristic peaks in the X-ray powder diffraction (XRPD) pattern at values of two theta (° 2θ) of 5.28, 8.96, 14.27, 16.18, 19.79, 21.16, 22.01, 23.31, 24.64, and 30.31.

14. The crystalline salt of claim 1, having an XRPD pattern substantially similar to that shown in FIG. 1.

15. The crystalline salt of claim 1, wherein the crystalline salt has a thermogravimetric-infrared spectrum substantially as shown in FIG. 2.

16. A pharmaceutical composition comprising the crystalline salt of claim 1; and one or more pharmaceutically acceptable carriers.

17. The pharmaceutical composition of claim 16, wherein the pharmaceutical composition is formulated for parenteral administration.

18. The pharmaceutical composition of claim 16, wherein the pharmaceutical composition is formulated for oral administration.

19. A method of treating or preventing a disease or condition characterized by aberrant plasma kallikrein activity, comprising administering to a subject in need thereof a therapeutically effective amount of a crystalline salt of claim 1.

20. The method of claim 19, wherein the disease or condition characterized by aberrant plasma kallikrein activity is selected from the group consisting of stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

21. The method of claim 20, wherein the disease or condition characterized by aberrant plasma kallikrein activity is angioedema.

22. The method of claim 20, wherein the disease or condition characterized by aberrant plasma kallikrein activity is hereditary angioedema.

23. The method of claim 20, wherein the disease or condition characterized by aberrant plasma kallikrein activity is stroke.

24. The method of claim 20, wherein the disease or condition characterized by aberrant plasma kallikrein activity is reperfusion injury.

25. The method of claim 20, wherein the disease or condition characterized by aberrant plasma kallikrein activity is acute myocardial infarction.

26. The method of claim 20, wherein the disease or condition characterized by aberrant plasma kallikrein activity is hemorrhage.

27. The method of claim 20, wherein the disease or condition characterized by aberrant plasma kallikrein activity is blood loss during cardiopulmonary bypass.

28. The method of claim 20, wherein the disease or condition characterized by aberrant plasma kallikrein activity is selected from the group consisting of retinopathy, diabetic retinopathy, diabetic macular edema, diabetic macular degeneration, age-related macular edema, age-related macular degeneration, and proliferative retinopathy.

* * * * *